United States Patent
Huitema et al.

(10) Patent No.: US 7,905,902 B2
(45) Date of Patent: Mar. 15, 2011

(54) SURGICAL IMPLANT WITH PREFERENTIAL CORROSION ZONE

(75) Inventors: Thomas W. Huitema, Cincinnati, OH (US); Gary W. Knight, West Chester, OH (US); Mark H. Ransick, West Chester, OH (US); Dale R. Schulze, Lebanon, OH (US)

(73) Assignee: Ethicon Endo-Surgery, Inc., Cincinnati, OH (US)

( * ) Notice: Subject to any disclaimer, the term of this patent is extended or adjusted under 35 U.S.C. 154(b) by 721 days.

(21) Appl. No.: 10/462,553

(22) Filed: Jun. 16, 2003

(65) Prior Publication Data
US 2004/0254608 A1 Dec. 16, 2004

(51) Int. Cl.
*A61B 17/064* (2006.01)

(52) U.S. Cl. .................. 606/220; 606/219; 606/232

(58) Field of Classification Search ............ 606/151, 606/154–156, 219–221, 75–77, 139, 141–143, 606/232, 322–331; 411/457, 476; 174/158 R, 174/159; 59/71–77; 227/175.1–182.1
See application file for complete search history.

(56) References Cited

U.S. PATENT DOCUMENTS

| | | | |
|---|---|---|---|
| 1,810,528 A * | 6/1931 | Peterson | 227/113 |
| 2,094,578 A | 10/1937 | Blumenthal et al. | |
| 3,347,239 A * | 10/1967 | Codling | 606/158 |
| 3,378,010 A | 4/1968 | Codling et al. | |
| 3,606,888 A * | 9/1971 | Wilkinson | 227/179.1 |
| 3,687,135 A | 8/1972 | Stroganov et al. | |
| 4,066,165 A * | 1/1978 | Ruskin | 206/340 |
| 4,263,903 A * | 4/1981 | Griggs | 606/75 |
| 4,278,091 A * | 7/1981 | Borzone | 606/75 |
| 4,407,286 A * | 10/1983 | Noiles et al. | 227/175.1 |
| 4,489,875 A * | 12/1984 | Crawford et al. | 227/19 |
| 4,602,632 A * | 7/1986 | Jorgensen | 606/158 |
| 4,655,222 A * | 4/1987 | Florez et al. | 606/219 |
| 4,719,917 A * | 1/1988 | Barrows et al. | 606/220 |
| 4,882,244 A * | 11/1989 | Donahue et al. | 429/339 |
| 4,889,119 A | 12/1989 | Jamiolkowski et al. | |
| 5,282,829 A * | 2/1994 | Hermes | 606/219 |
| 5,522,836 A * | 6/1996 | Palermo | 606/200 |
| 5,584,856 A * | 12/1996 | Jameel et al. | 606/220 |
| 5,788,698 A * | 8/1998 | Savornin | 606/75 |
| 5,891,128 A | 4/1999 | Gia et al. | |
| 6,030,637 A * | 2/2000 | Whitehead | 424/438 |
| 6,066,144 A | 5/2000 | Wolf et al. | |
| 6,099,562 A * | 8/2000 | Ding et al. | 623/1.46 |
| 6,287,332 B1 * | 9/2001 | Bolz et al. | 623/1.15 |

(Continued)

OTHER PUBLICATIONS

J.L. Sandrik, E.H. Greener, and L.E. Wragg; Tissue Reaction and In Vivo Corrosion of Ferrous Alloy Implants, Article, pp. 125-133, Northwestern University, Chicago, Illinois.

(Continued)

*Primary Examiner* — Anhtuan T Nguyen
*Assistant Examiner* — Kathleen Sonnett (57) ABSTRACT

The present invention provides a surgical implant which can be made of a metal that corrodes while implanted in tissue of a patient. The surgical implant has a preferential corrosion zone adapted to corrode at a different rate than the rest of the surgical implant. In one embodiment, the surgical implant is surgical staple that may be formed into a "B-shape" when deployed into tissue, although the invention also is applicable to many other kinds of staples, clips, and other metallic surgical implants. In one embodiment, the preferential corrosion zone comprises an indentation that provides a site for crevice corrosion.

11 Claims, 7 Drawing Sheets

U.S. PATENT DOCUMENTS

| | | | |
|---|---|---|---|
| 6,325,810 B1 * | 12/2001 | Hamilton et al. | 606/151 |
| 2002/0004060 A1 | 1/2002 | Heublein et al. | |
| 2002/0051695 A1 | 5/2002 | Friederich et al. | |
| 2004/0006372 A1 * | 1/2004 | Racenet et al. | 606/219 |
| 2004/0092937 A1 | 5/2004 | Criscuolo et al. | |
| 2004/0167572 A1 * | 8/2004 | Roth et al. | 606/219 |
| 2004/0254608 A1 | 12/2004 | Huitema et al. | |
| 2006/0052824 A1 | 3/2006 | Ransick et al. | |

OTHER PUBLICATIONS

Charles S. Vanable, M.D., Walter G. Stuck, M.D., and Asa Beach, M.D., The Effects on Bone of the Presence of Metals Based upon Electrolysis, Annals of Surgery, Jun. 1937, pp. 917-938, San Antonio, Texas.

* cited by examiner

SURGICAL IMPLANT WITH PREFERENTIAL CORROSION ZONE

FIELD OF THE INVENTION

The present invention relates, in general, to the field of surgery and, more particularly, to surgical implants made of metal.

BACKGROUND

Surgeons implant a wide variety of metallic, ceramic, and polymeric materials into patients. Surgeons use metallic implants primarily for orthopedic purposes, but additional applications include wound closure (internal and external), reconstructive surgery, cosmetic surgery, wire leads, heart valve parts, aneurysm clips, and dental uses. Because metals have favorable mechanical properties, including elasticity, deformability, and stability, metallic implants are generally less bulky than their non-metallic counterparts—an important precondition for application to minimally invasive surgery. Metallic implants must withstand and function within the body environment at least for a certain period of time. Therefore, the rate and type of structural degradation, via corrosion and other processes while in vivo, is an important consideration in the design of surgical implants. In addition, corrosion of metallic implants is an important consideration for biocompatibility, due to the release of metal ions into the body environment.

Some of the metals currently used for surgical implants include stainless steel (AISI type 316L), cobalt-chromium-molybdenum-carbon, cobalt-chromium-tungsten-nickel, cobalt-nickel-chromium-molybdenum, titanium, Ti-6Al-4V, Ti-3Al-2.5V, and tantalum. These metals transition from an active to a passive state by developing a protective surface oxide film when used as implants and are highly corrosion resistant in saline environments such as in the body.

The body recognizes surgical implants as foreign objects, potentially leading to local and possibly systemic reactions. Permanent metallic implants are particularly undesirable for young patients because retention for decades is unavoidable. Some metallic implants including, for example, surgical staples, clips, and vascular stents, may be constructed of metals that corrode quickly in the body. The corrosion by-products are harmlessly absorbed by the body or passed through the digestive system. For example, a surgical staple made from commercially pure iron may corrode in animal soft tissue within a few weeks, but the staple would have sufficient structural integrity for a long enough period of time, usually several days, to allow healing of the tissues involved. The surgical staple may also be made of other absorbable metals, including carbon steel. The absorption of small amounts of corrosion by-products (for iron or carbon steel, the primary by-product is iron oxide or rust,) is not known to have any significant, deleterious effect on the body. The ferromagnetic property of iron and carbon steel is a factor relative to their compatibility with MRI (magnetic resonance imaging), although the very small mass of some implants, such as surgical staples, and the very short time they are present in the body before corroding and being absorbed, allows the beneficial use of such materials. Other benefits of absorbable staples include reducing scatter on X-ray images, minimizing future adhesions, and avoiding staple lines in future surgical procedures.

Corrosion is primarily the result of an electrochemical reaction of a metal with its environment and occurs because the metal oxide or corrosion product is more stable thermodynamically than the metal. Electrochemical deterioration of the metal occurs as positive metal ions are released from the reaction site (anode) and electrons are made available to flow to a protected site (cathode). The electrochemical reaction cell consists of two conducting and electrically connected electrodes in an electrolytic solution. The two electrodes can be dissimilar metals, or they can result from different surface areas of the same metal, defects, impurities, precipitate phases, concentration differences of gas, solution or metal ions, or other variables. The rate at which the corrosion reaction proceeds is primarily related to environmental composition and effects, such as motion or load. The physiological environment in the human body contains chloride ions (Cl−) and is controlled at a pH level of 7.4 and a temperature of 37 degrees C. (98.6 degrees F.). Following surgery, the pH can increase to 7.8, decrease to 5.5, and then return to 7.4 within a few weeks. These variations are caused by infection, hematoma, and physiological solutions administered during and after surgery.

Corrosion resistance of a metal is specific to a number of factors, including composition, changes in metallurgical heat treatment, microstructural phases present, and surface finish. The rate of corrosion of a metal can be slowed or halted by applying a coating, such as a moisture barrier, that shields the metal from the corrosive environment. Conversely, creating an even harsher corrosive environment can accelerate the corrosion rate of a metal. In addition, it is possible to cause the corrosion process to be focused on a localized area of the metal. By using these principles and biasing the corrosion process to take place at a desired rate and/or at a desired location of the metal, it is possible to design a metallic, surgical implant that corrodes within the body in a beneficial manner.

Each of the many surgical implants that may be made from an absorbable metal has a shape that is designed specifically for its deployment into tissue and its initial, primary function, such as holding tissue layers together during wound healing. As the implant corrodes, the ability of the implant to perform its primary function degrades. Biasing the corrosion rate and location on the implant allows the implant to fragment in a desirable way during the early stages of the corrosion process. For example, physical attributes of the implant important for deployment into tissue are not necessarily desirable thereafter while implanted in the body. The sharp tips of a surgical staple are necessary for penetration into tissue during deployment, but can cause prolonged pain or irritation to the patient thereafter. Procedures with such post-surgical complaints by patients include inguinal hernia repair and hysterectomy (in which a male sexual partner experiences the discomfort.) Also, in some situations, it would be advantageous for the implant to corrode in a specific manner, so that the ability of the implant to perform its primary function even improves. For example, surgical staplers commonly referred to in the art as circular staplers are used to perform an end-to-end or end-to-side anastomosis of hollow organs such as the large or small intestines. The surgeon uses the circular stapler to deploy a plurality of tiny, surgical staples evenly spaced apart in a pair of concentric circular staplelines (or more simply, "staple circles") around a lumen, in order to connect the two organs together in fluid communication. Each staple is formed into a "B-shape" to clinch tissue layers together. A ring of relatively inelastic scar tissue forms over these staple circles. By using surgical staples that initially corrode and fragment from "B-shapes" into "two half B-shapes", the primary tissue holding function of the staples is not compromised, yet the staple circles are more flexible and easily dilated.

What is needed, therefore, is a surgical implant made of a metal that corrodes and becomes absorbed in the body without compromising the primary function of the implant, and the rate of corrosion on at least a portion of the implant is alterable in order to provide benefit to the patient.

SUMMARY

The present invention is a surgical implant made of a metal that corrodes while implanted in the tissue of a patient, and the surgical implant has a preferential corrosion zone adapted to corrode at a different rate than the rest of the surgical implant. For the embodiments described herein, the surgical implant is illustrated as a surgical staple that may be formed into a "B-shape" when deployed into tissue, although the present invention also is applicable to many other kinds of staples, clips, and other metallic surgical implants.

In one embodiment, the preferential corrosion zone comprises an indentation that provides a site for crevice corrosion.

In another embodiment, the surgical implant has a coating over at least a portion of its surface, and the preferential corrosion zone comprises an uncoated region. The coating may be, but is not limited to, one of the following: parylene, sodium stearate, calcium stearate, polytetrafluoroethylene, polyurethane, polyethylene, polypropylene, and polyethylene teraphthalate, gold, and silver.

In another embodiment, the surgical implant develops the preferential corrosion zone during deployment of the surgical implant into the tissue of the patient. In one version of this embodiment, the preferential corrosion zone comprises a coating that develops a plurality of cracks or otherwise becomes altered during deployment of the surgical implant, thereby exposing at least a portion of the metal of the surgical implant to the tissue of the patient.

In a further embodiment, the surgical implant is a surgical staple that is deployable together and in physical contact with a buttress into the tissue of the patient, and the preferential corrosion zone comprises an interface between the surgical staple and the buttress. In one version of this embodiment, the buttress contains a corrosion promoting material that increases the electrochemical corrosion rate in the preferential corrosion zone of the surgical staple. In another version of this embodiment, the buttress is cathodic with respect to the surgical staple, and the surgical staple galvanically corrodes at an interface between the buttress and the surgical staple.

In all of the aforementioned embodiments, the surgical implant may comprise various metals, including without limitation: commercially pure iron; low carbon steel; medium carbon steel; high carbon steel; an alloy whose main constituent is selected from the group consisting of an alkali metal, an alkaline earth metal, iron, zinc, or aluminum; and combinations thereof. As used herein "commercially pure iron" means at least about 99.85 percent by weight Fe, no more than 0.06 percent by weight carbon, the balance impurities and/or trace elements. In one embodiment, the surgical implant can be formed of commercially pure iron comprising at least 99.995% Fe. As used herein "low carbon steel" means carbon steel comprising less than about 0.30 percent by weight carbon. As used herein "medium carbon steel" means carbon steel comprising between about 0.30 and about 0.85 percent by weight carbon. As used herein "high carbon steel" means carbon steel comprising more than about 0.85 percent by weight carbon and less than about 2.0 percent by weight carbon. The surgical implant may also be formed of ductile iron having from about 3.5 to about 4.5 percent carbon content by weight. All percentages are by weight unless otherwise indicated.

DETAILED DESCRIPTION OF THE INVENTION

The present invention is a surgical implant made, at least in part, of a metal that corrodes and is absorbed within a patient, and at least one portion of the surgical implant, hereinafter referred to as a preferential corrosion zone, is adapted to corrode at a different rate than the remaining portion(s). Those skilled in the art may adapt the present invention to various surgical implants, including surgical clips, staples, stents, bone anchors, and generally, for metal surgical implants for which it is advantageous to the patient to cause the surgical implant to degrade, fragment, or physically reconfigure in a particular manner while in a patient. Exemplary embodiments of the present invention include various types of surgical staples, for which a detailed description follows.

Each of the embodiments of surgical staples described herein is made of a metal that electrochemically or galvanically corrodes upon prolonged exposure to the environment in live body tissues and fluids. The surgical staple is made of a metal that corrodes and becomes absorbed by the body during a predetermined period of time typically ranging from approximately four to ten weeks. Numerous metals are suitable for the present invention and include iron, carbon steel, or an alloy whose main constituent is an alkali metal, an alkaline earth metal, iron, zinc, or aluminum. The surgical staple may be made from commercially pure iron wire. In one embodiment, the surgical staple may be formed of commercially pure iron wire comprising about 99.995% iron, about 100 ppm (parts per million) of oxygen, and only traces (less than 10 ppm) of other elements, including cobalt, nickel, silicon, and sulfur. The surgical staple may also be made of an iron containing alloy containing, for example, 0.05% to 7% by weight carbon. Carbon steel is known to corrode in an aqueous environment as fast or faster than commercially pure iron, but is generally less ductile and harder to draw into wire. Pure iron also work hardens well and has little "spring back," which are desirable characteristics for surgical staples that are formed into a "B-shape" as will be described.

Figure 1:
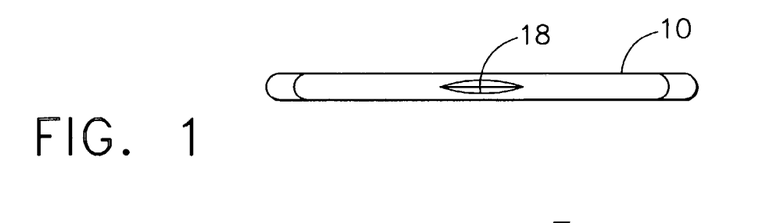
FIG. 1 is a top view of a first embodiment of the present invention, a surgical staple 10 having an indentation 18 on a crown 10.
Figure 2:
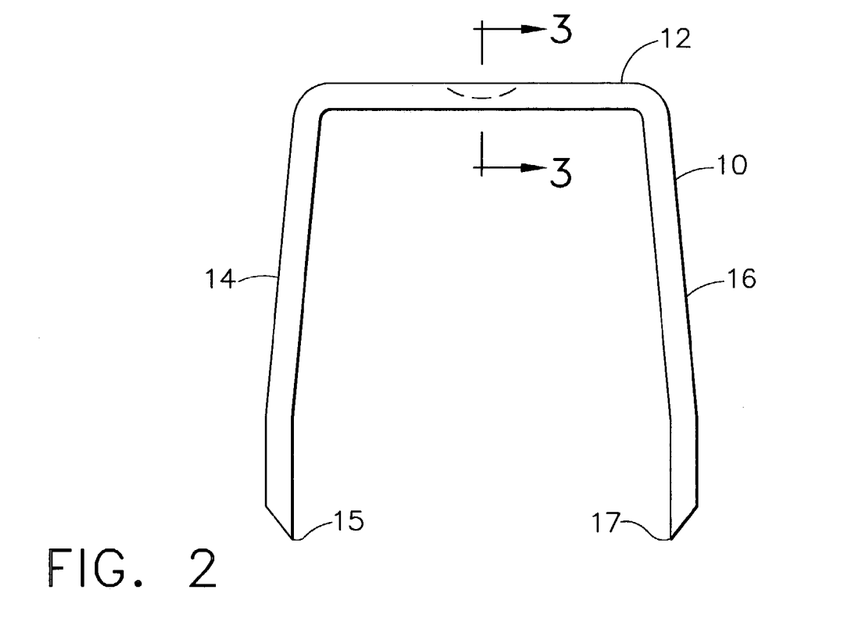
FIG. 2 is a front view of surgical staple 10 shown in FIG. 1.
Figure 3:
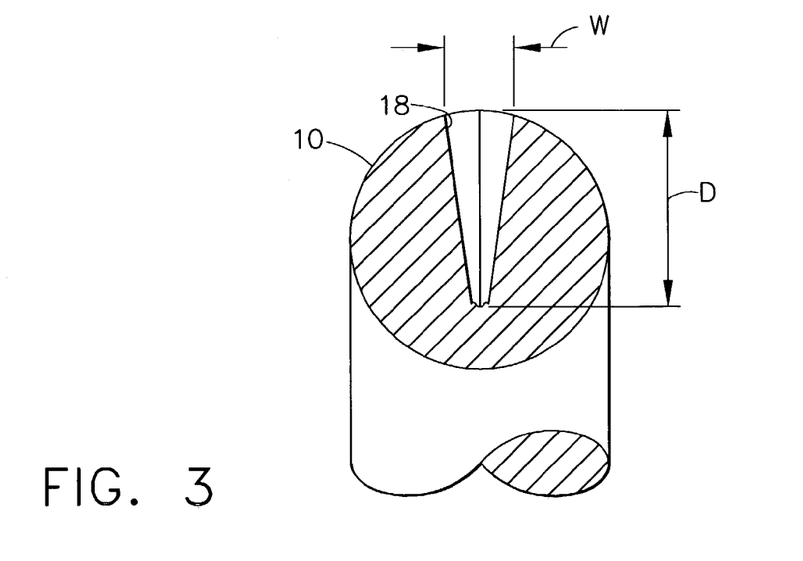
FIG. 3 is a cross sectional view taken at line 3-3 of FIG. 2 of crown 10.

FIG. 1 shows a top view and FIG. 2 shows a front view of a first embodiment of the present invention, a surgical staple 10, in a preformed configuration. Staple 10 can be made from 0.279 mm (0.011 inch) diameter wire and comprises a first leg 14, a second leg 16, connected by a crown 12. First leg 14 and second leg 16 can each be approximately 5.51 mm (0.217 inches) long. Crown 12 can be approximately 3.96 mm (0.156 inches) wide. First leg 14 has a first tip 15 and second leg 16 has a second tip 17. In the embodiment in FIGS. 1-3, an indentation 18 can be provided which is located approximately in the middle of crown 12. Indentation 18 may be coined into crown 12 as staple 10 is formed from straight wire on a staple making and loading machine, as may be easily envisioned by those skilled in the art. The coining step may be a closed-die forging operation performed cold, in which all surfaces of the wire are restrained, resulting in a well-defined imprint of the die in crown 12. FIG. 3 shows a cross-section of staple 10 taken at line 3-3 of FIG. 2.

In the embodiment shown, indentation 18 has a width W and a depth D and comprises a preferential corrosion zone when staple 10 is implanted in tissue of a patient. Width W can be about 0.05 to about 0.100 mm wide and depth D may extend into staple 10 about 0.05 to about 0.20 mm deep. Indentation 18 may also have many other configurations or orientations and still comprise a preferential corrosion zone on staple 10. In general, indentation 18 can be provided to be generally wide enough to permit liquid entry, but sufficiently narrow to maintain a stagnant zone. Staple 10 may also include more than one preferential corrosion zone similar to indentation 18 and located on other parts of staple 10.

Figure 6:
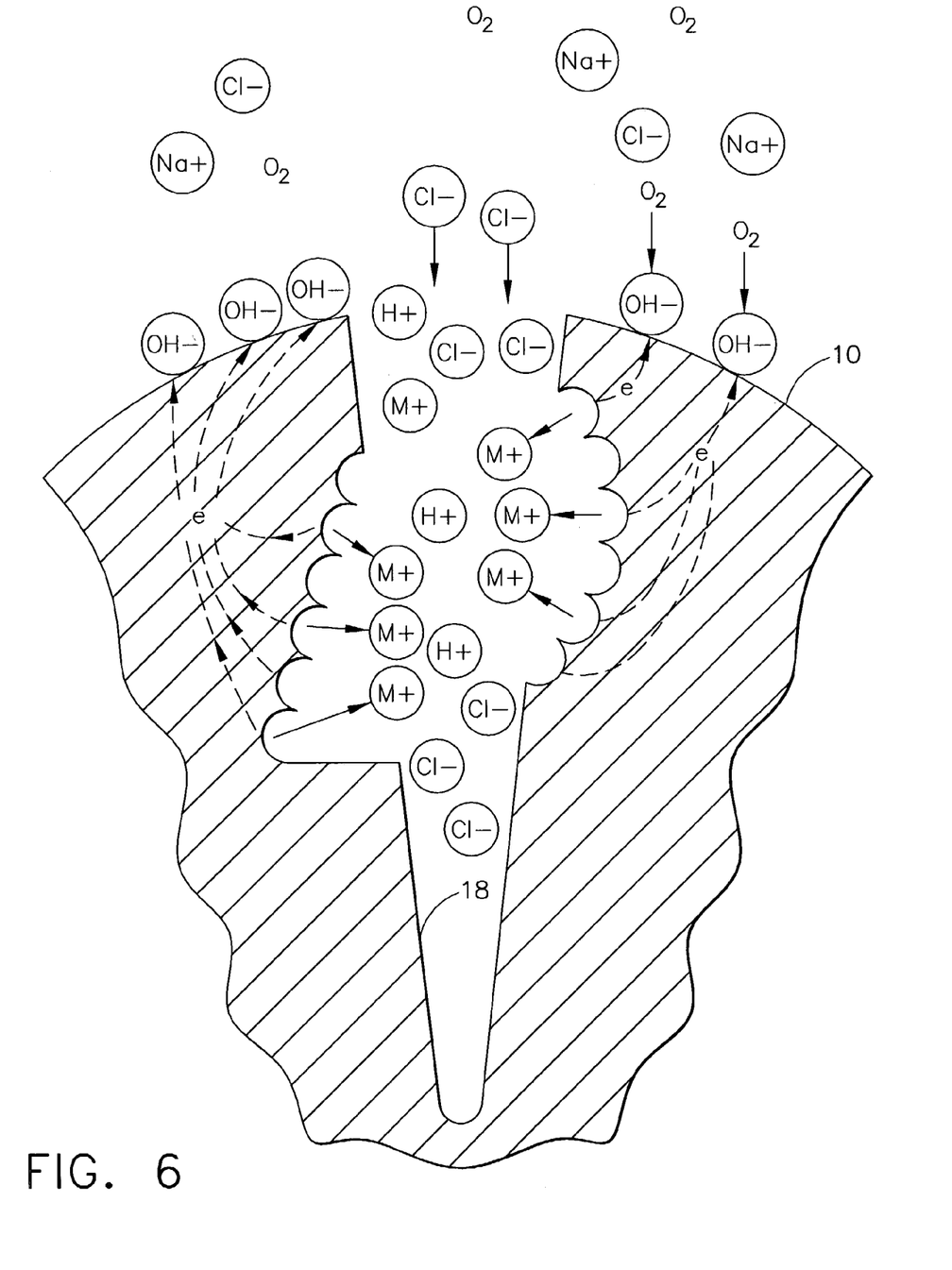
FIG. 6 is a representation of the crevice corrosion process occurring within indentation 18 of surgical staple 10.

Without being limited by theory, it is believed that FIG. 6 provides a schematic representation of the electrochemical process of crevice corrosion that occurs at indentation 18 of staple 10. The overall reaction involves the dissolution of metal M and the reduction of oxygen to hydroxide ions:

Oxidation $M \rightarrow M_+ + e$

Reduction $O_2 \rightarrow 2H_2O + 4e \rightarrow 4OH-$

Initially, these reactions occur uniformly over the entire surface, including the interior of indentation 18. Charge conservation is maintained in both the metal and solution. Every electron produced during the formation of a metal ion is immediately consumed by the oxygen reduction reaction. Also, one hydroxyl ion is produced for every metal ion in the solution. After a short interval, the oxygen within indentation 18 is depleted because of the restricted convection, so oxygen reduction ceases in this area, but the dissolution of metal M continues as shown in FIG. 6. This tends to produce an excess of positive charge (M+) in indentation 18, which is necessarily balanced by the migration of chloride ions (Cl−), which are naturally abundant in body fluids, into indentation 18. This results in an increased concentration of metal chloride within indentation 18, which hydrolyzes in water:

$M_+Cl- + H_2O = MOH + H_+Cl-$

An aqueous solution of a typical metal chloride dissociates into an insoluble hydroxide and a free acid. Both chloride and hydrogen ions accelerate the dissolution rates of most metals. These are both present in indentation 18 as a result of migration and hydrolysis, consequently the dissolution rate of M is increased, thus increasing migration, and the result is a rapidly accelerating, or autocatalytic, process. Once crevice corrosion has started, it proceeds at an ever-increasing rate. Staple 10 corrodes and breaks apart at the preferential corrosion zone (indentation 18) first, before any other portion of staple 10 fragments. Therefore, it is possible to cause staple 10 to degrade and fragment in an advantageous manner, as will be described.

Figure 4:
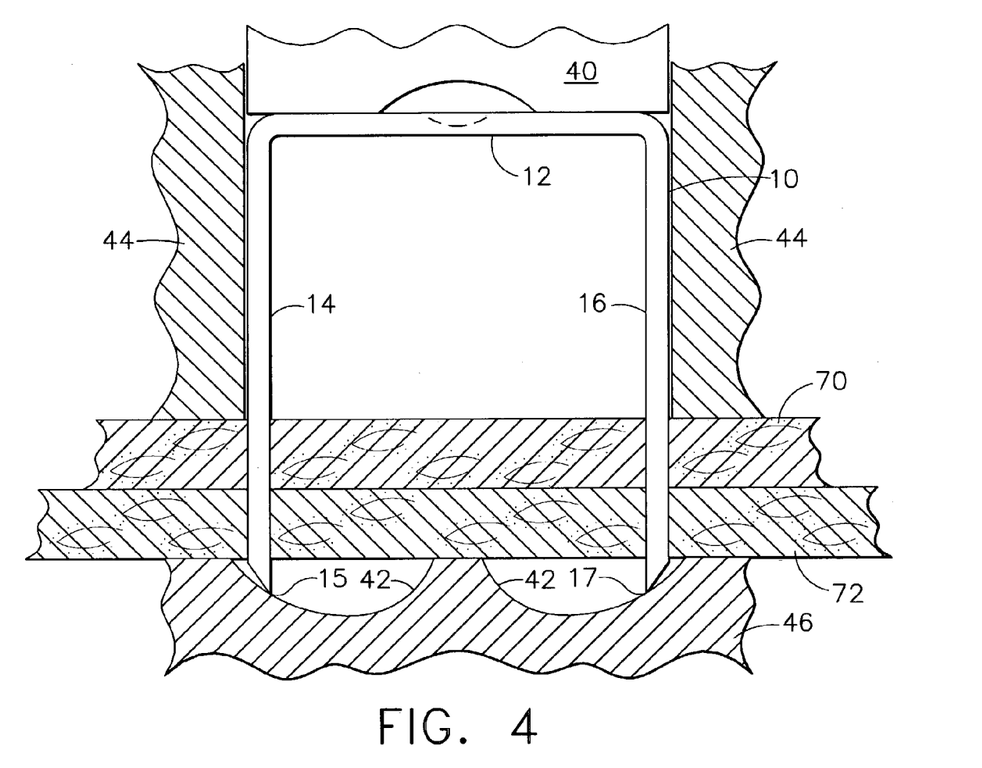
FIG. 4 shows surgical staple 10 in a pre-formed configuration and penetrated into a first tissue layer 70 and second tissue layer 72.
Figure 5:
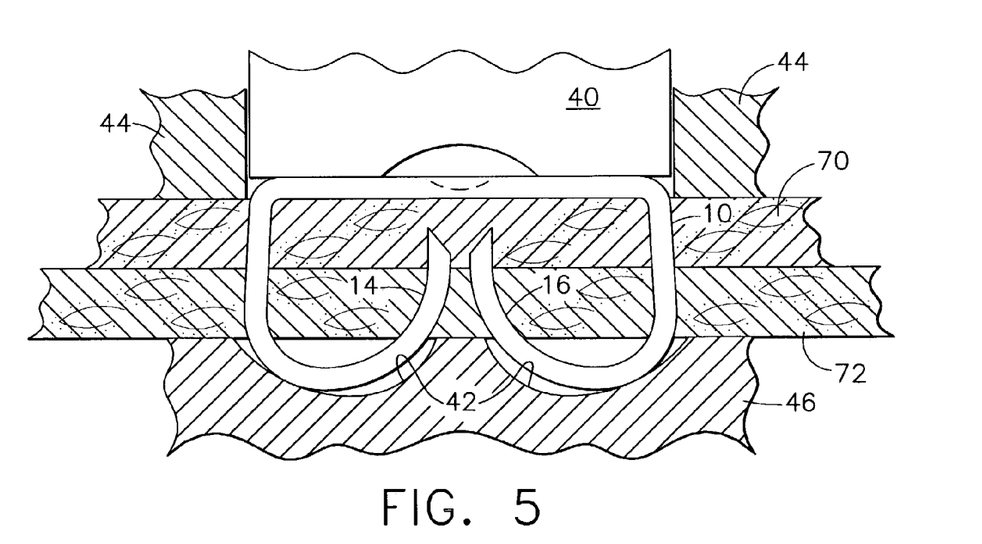
FIG. 5 shows surgical staple 10 in a formed configuration for fastening first tissue layer 70 and second tissue layer 72 together.

FIG. 4 shows staple 10 in a preformed configuration as a driver 40 pushes (downward) against crown 12 of staple 10 to move staple 10 out of a cartridge 44. First and second staple legs, 14 and 16, are approximately parallel when contained in cartridge 44. As driver 40 pushes staple 10, first and second tips, 15 and 17, penetrate through a first tissue layer 70 and a second tissue layer 72, and slide against an anvil pocket 42 coined into an anvil 46. As shown in FIG. 5, driver 40 pushes crown 12 against first tissue layer 70 and ejects staple 10 from cartridge 44. First and second legs, 14 and 16, curl inward to form a "B-shape" that tightly clinches together first and second tissue layers, 70 and 72. This B-shape is also referred to as a formed configuration.

Surgical staplers typically deploy a plurality of surgical staples into tissue, where the staples are spaced apart in parallel staple lines or concentric staple circles. For example, the CDH25 Circular Surgical Stapler (Ethicon Endo-Surgery, Inc., Cincinnati, Ohio) deploys ten evenly spaced-apart staples in each of two concentric staple circles, for creating an end-to-end bowel anastomosis having a lumen diameter of approximately 25 mm.

Figure 11:
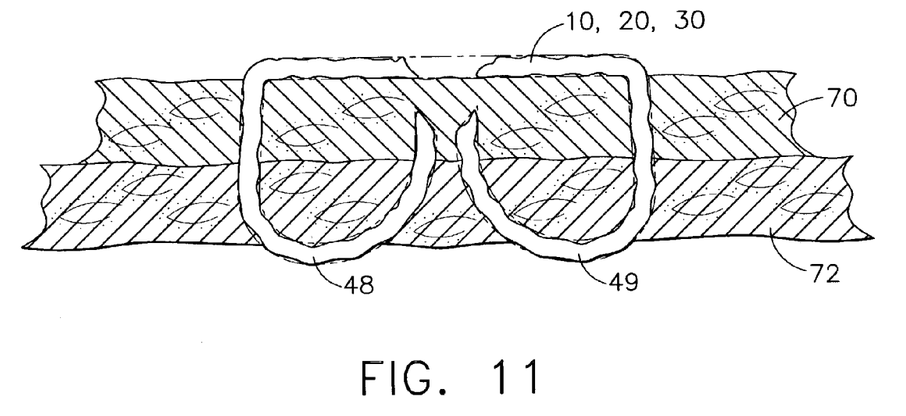
FIG. 11 shows surgical staple 10, 20, or 30 after being implanted in a patient for a period of time.

FIG. 11 shows staple 10 as it may appear after being implanted in the body for several days. Corrosion has been most aggressive in the preferential corrosion zone, resulting in the fragmentation of staple 10 from a "B-shape" to a first and a second "half B-shape," 48 and 49. Each of first and second half-B-shapes, 48 and 49, fully encloses tissue and still functions to clinch first and second tissue layers, 70 and 72, together during healing. The accumulative effect of a plurality of staples fragmenting as shown in FIG. 11 results in the ability of the staple circles to be flexed and stretched with less force than if the staple circles comprised conventional staples made of stainless steel or titanium alloy. This improves the ability of the bowel stricture to gradually relax via passage of matter, even before the entire staple 10 is completely corroded and absorbed by the body. This manner of fragmentation also reduces the force required to surgically dilate the bowel stricture. In a dilation procedure, a surgeon passes progressively larger diameter surgical dilators through the bowel stricture to radially stretch the ring of scar tissue formed over the staple circles of the anastomosis.

Figure 7:
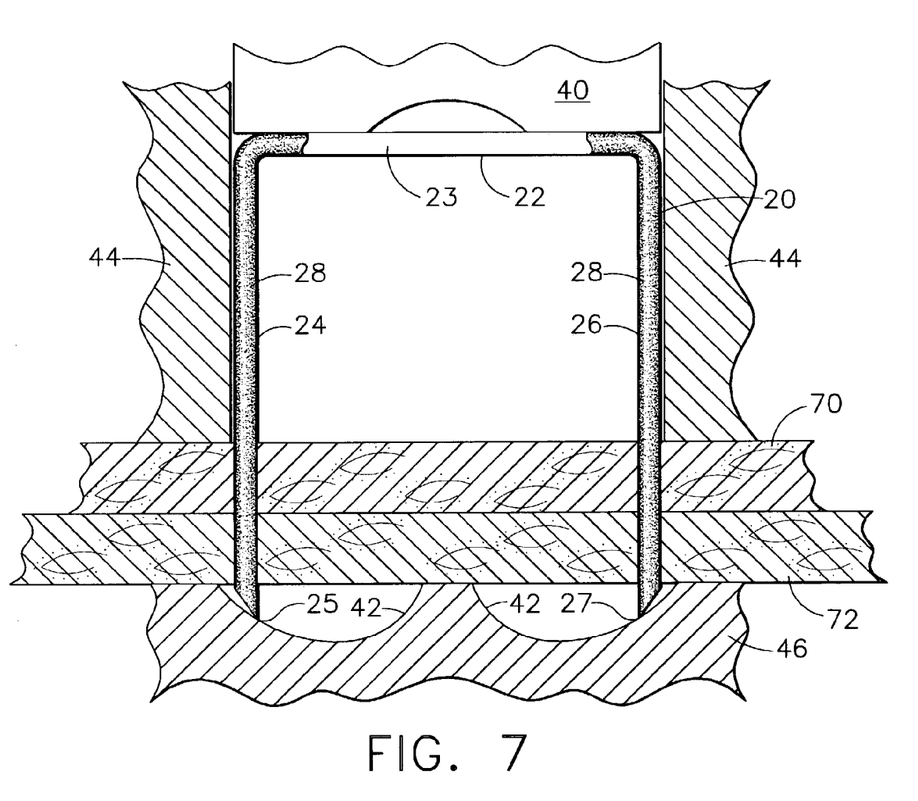
FIG. 7 shows a second embodiment of the present invention, a surgical staple 20, which is partially coated with a coating 28, in a pre-formed configuration and penetrated into first tissue layer 70 and second tissue layer 72.

FIG. 7 shows a second embodiment of the present invention, a staple 20, having a first leg 24 with first tip 25, a second leg 26 with tip 27, and a crown 22. Staple 20 may be made from the same metal wire material and have the same overall dimensions as staple 10 of FIG. 4. Staple 20 has a coating 28, however, covering first and second legs, 24 and 26. An uncoated region 23 of crown 22 is a preferential corrosion zone in this embodiment. Coating 28 is a temporary moisture barrier that eventually dissolves, deteriorates, degrades, breaks apart, or generally delays the start or decreases the rate of the corrosion of staple 20. Coating 28 may be made from any one of several commercially available, biocompatible coating materials known in the art including calcium stearate, sodium stearate, parylene, polytetrafluoroethylene or other fluoropolymers, polyurethane, polyethylene, polypropylene, polyethylene teraphthalate, or other known suitable, typically polymeric material. Coating 28 may also be made of a more noble metal, such as gold. Coating 28 may be applied to selected portions of staple 20 using conventional dipping, spraying, masking, or vapor deposition techniques known in the art. Coating 28 may also be applied to the entire surface of staple 20, and then a portion of coating 28 may be removed from crown 22 to create a preferential corrosion zone using a high energy laser, mechanical abrasion, chemical dissolution, or other known coating removal techniques.

Figure 8:
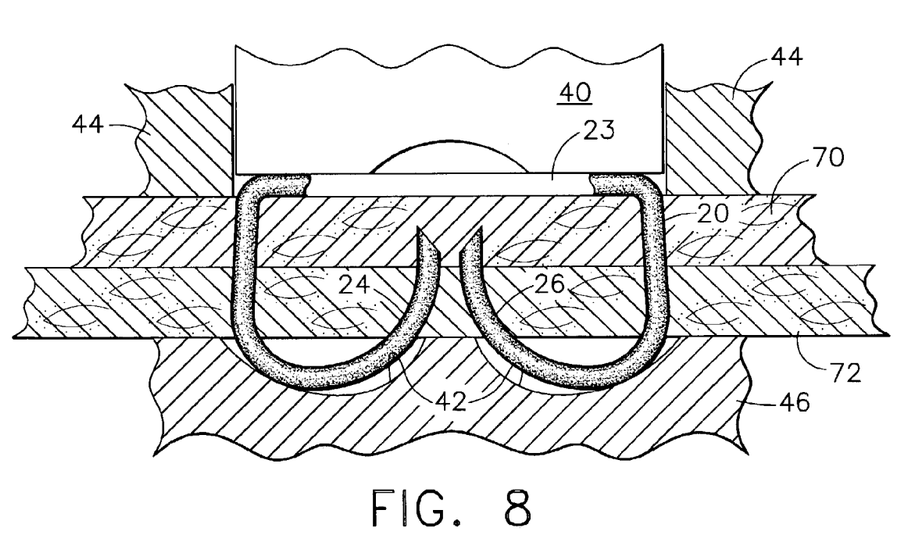
FIG. 8 shows surgical staple 20 in a formed configuration for fastening first tissue layer 70 and second tissue layer 72 together.

FIG. 7 shows staple 20 in a preformed configuration as driver 40 pushes staple 20 out of cartridge 44 so that first and second tips, 25 and 27, penetrate first and second tissue layers, 70 and 72, and strike against anvil pocket 42 of anvil 46. FIG. 8 shows staple 20 in a formed configuration, a "B-shape" that clinches first and second tissue layers, 70 and 72, tightly together. Staple 20 corrodes electrochemically much more rapidly at uncoated region 23, the preferential corrosion zone, than on first and second legs, 24 and 26, which are covered with coating 28. Thus within several days, staple 20 fragments as shown in FIG. 11, resulting in a first and second "half-B-shape" as for the previous embodiment.

Figure 9:
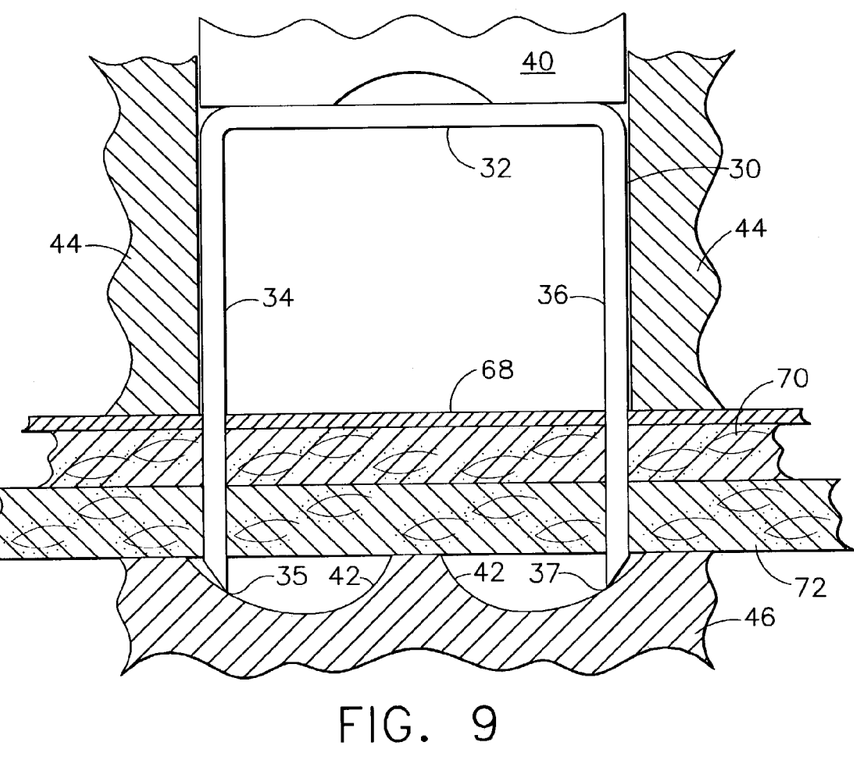
FIG. 9 shows a third embodiment of the present invention, a surgical staple 30 combined with a buttress material 68, in a pre-formed configuration and penetrated into first tissue layer 70 and second tissue layer 72.
Figure 10:
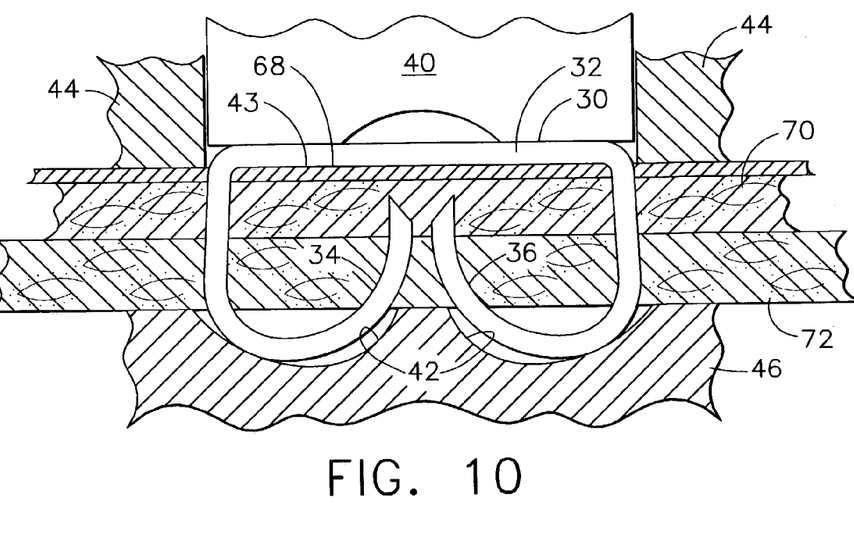
FIG. 10 shows surgical staple 30 and buttress material 68 in a formed configuration for fastening first tissue layer 70 and second tissue layer 72 together.

FIG. 9 shows a third embodiment of the present invention, a staple 30 combined with a buttress 68. Staple 30 may be made of the same absorbable metal and have the same physical dimensions as staple 10 of FIG. 4. Driver 40 pushes staple 30 out of cartridge 44, and first and second tips, 35 and 37, penetrate buttress 68, first tissue layer 70, second tissue layer 72, and strike against anvil pocket 42 of anvil 46. FIG. 10 shows staple 30 in a formed configuration, a "B-shape" that tightly clinches together first and second tissue layers, 70 and 72, and buttress 68. Crown 32 of staple 30 tightly abuts buttress 68, forming an interface 43. Buttress 68 may be a sheet of material removably attached to the tissue-contacting surface of cartridge 44 with a biocompatible adhesive or by an equivalent method, thus covering the plurality of staple pockets in the cartridge and helping to retain the staples prior to deploying the staples into tissue. When the plurality of staples is deployed into tissue, attaching buttress 68 to first tissue layer 70, buttress 68 easily detaches from cartridge 44 as the stapling device holding cartridge 44 is pulled away from the tissue. Buttress 68 may be made of any one of several different materials, depending on the type and speed of corrosion desired. For example, buttress 68 may be made from an absorbable material such as Vicryl (Ethicon, Inc., Somerville, N.J.), which has been soaked in a saline solution and dried prior to assembly with cartridge 44. The sodium chloride film remaining on the material promotes corrosion of staple 30 when implanted in moist tissue, especially on the buttress side of the tissue, so that crown 32 corrodes preferentially. Buttress 68 may also be made of a relatively unabsorbable material, such as a fabric made with a natural or synthetic fiber, wherein the unabsorbable material also contains a substance that promotes or inhibits corrosion of metal in an aqueous environment. Buttress 68 may also be made of a paper containing the corrosion promoting or inhibiting substance, which becomes active only when implanted into tissue. The paper may also act as a desiccant during the storage of the cartridge and staples in a moisture impermeable package, in order to prevent corrosion of the staples during the shelf life of the product. Buttress 68 may also be made of a biological material such as bovine pericardium, which again has been treated with a corrosion promoting or inhibiting agent. Buttress 68 may also contain a material that is cathodic to the material of staple 30. If staple 30 is made of pure iron or carbon steel, buttress 68 may be a polymeric film laminated or coated with a thin layer of gold, tantalum, titanium, or carbon. When staple 30 is implanted into tissue so that buttress 68 is in contact with crown 32, staple 30 is anodic with respect to buttress 68. Interface 43 of staple 30 becomes a preferential corrosion zone comprising a plurality of localized anodic regions and interfaces that would corrode first. Within several days, staple 30 would fragment as shown in FIG. 11, providing the same clinical benefits as described for the previous embodiments. Depending on material selection, buttress 68 may remain permanently in the tissue, either intact or fragmented, or may disintegrate and become absorbed by the body after functioning to provide a preferential corrosion zone at interface 43 of staple 30. Buttress 68 also provides an additional function, as the name implies, of reinforcing the staple line or circle with a layer of tough material to back the soft tissue layers. A buttress material may be used with a surgical stapler to improve hemostasis and healing at the wound site.

Figure 12:
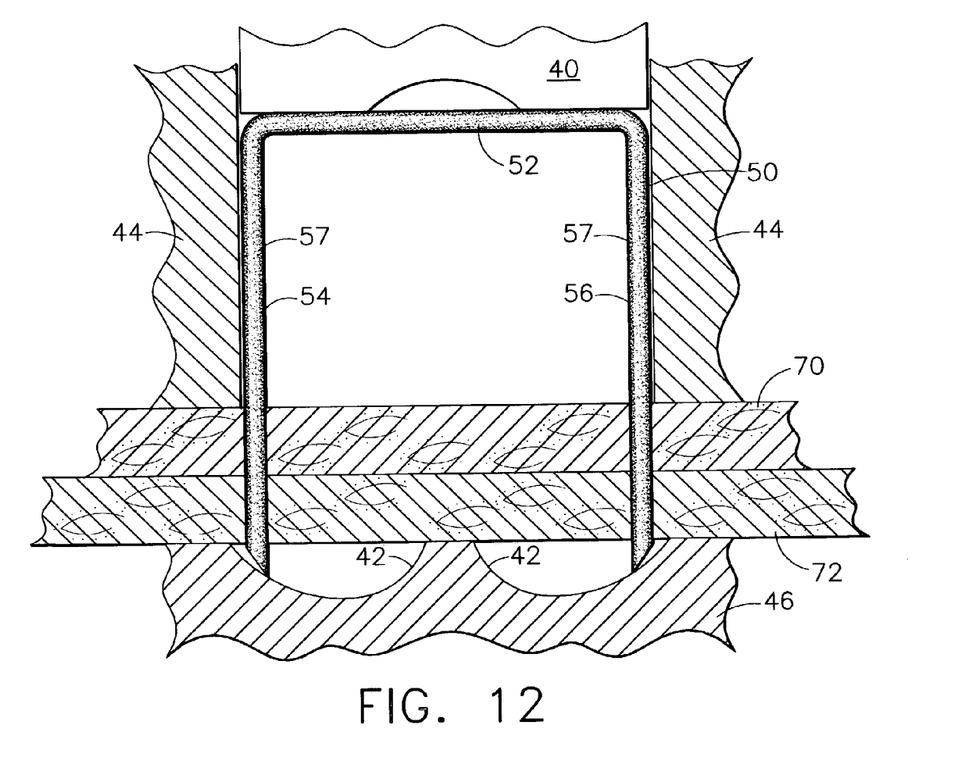
FIG. 12 shows a fourth embodiment of the present invention, a surgical staple 50, which is completely coated with a coating 57, in a pre-formed configuration and penetrated into first tissue layer 70 and second tissue layer 72.

FIG. 12 shows a fourth embodiment of the present invention, a staple 50 that is completely covered with a coating 57. Coating 57 may be made of any one of the same materials described for staple 20 of FIG. 7, but preferably is made of a material that either is brittle and tends to crack easily when flexed, or is easily removable by frictional contact with anvil pocket 42 of anvil 46 during formation of staple 50 into a formed configuration. Parylene is particularly suited for coating 57 because it is biocompatible, brittle, and may easily be applied to a desired thickness onto surgical staples by vapor deposition. Parylene also is an excellent electrical insulator and provides a benefit of allowing the implanted staple line or circle to be compatible with electrosurgical instruments. For example, if a physician touches the active tip of a monopolar, electrosurgical instrument to a non-insulated, metallic object (such as a conventional surgical staple) in the body, the energy of the instrument may be redirected to an area of the tissue that the physician does not intend to treat.

Still referring to FIG. 12, driver 40 pushes a crown 52 of staple 50 to advance first and second legs, 54 and 56, through first and second tissue layers, 70 and 72.

Figure 13:
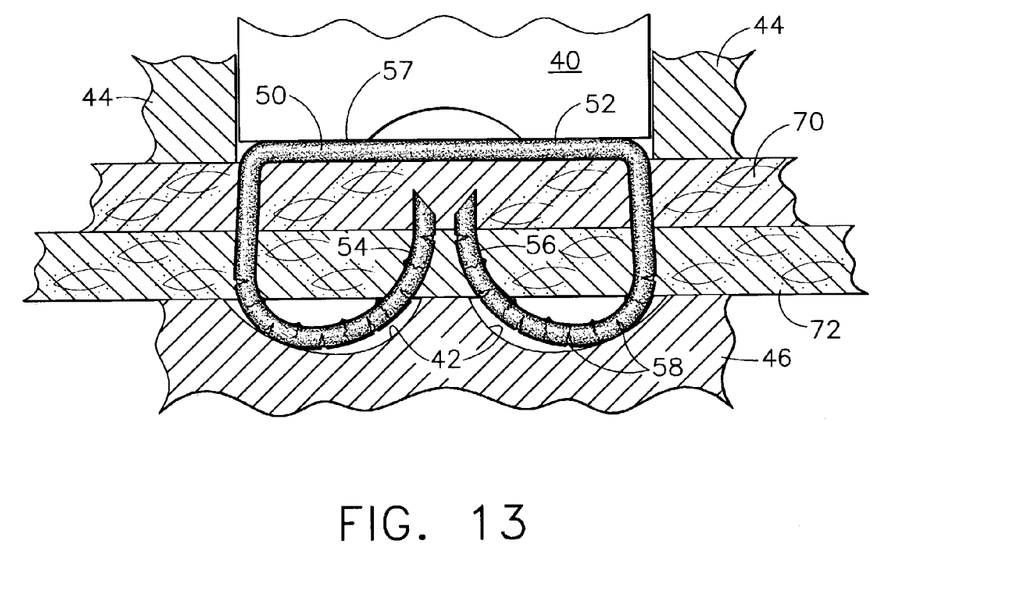
FIG. 13 shows surgical staple 50 in a formed configuration for fastening first tissue layer 70 and second tissue layer 72 together.
Figure 14:
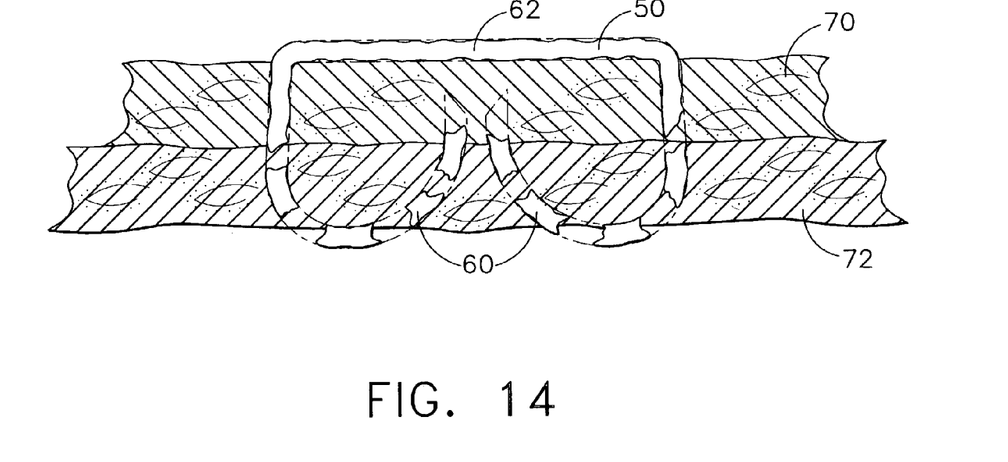
FIG. 14 shows surgical staple 50 after being implanted in a patient for a period of time.

FIG. 13 shows staple 50 in the formed configuration, the conventional "B-shape" as described for previous embodiments. Coating 57 is shown as developing a plurality of cracks 58 on the portions of first and second legs, 54 and 56, which are bent during the staple formation process. Cracks 58 expose the metal wire material of staple 50 to the corrosive environment in the tissue. First and second legs, 54 and 56, thus become preferential corrosion zones, and corrode more rapidly than crown 52. FIG. 14 shows how staple 50 may corrode and fragment after staple 50 has been implanted in tissue for several days. This mode of staple degradation may be desirable when the presence of staple tips may cause discomfort to the patient (as previously described for some types of inguinal herniorrhaphy or to a sexual partner (as previously described for laparoscopic assisted vaginal hysterectomy.)

When staple 50, shown in FIG. 12, is in the pre-formed configuration, coating 57 is still an effective moisture barrier. Coating 57 is only an ineffective moisture barrier once staple 50 has been deployed into tissue, and staple 50 is in the formed configuration. Therefore, the metal wire material of staple 50 is protected from corrosion during the later stages of manufacture and the shelf life of the device that contains staple 50. The number of months or years between manufacture of staple 50 and actual deployment into tissue would not significantly affect the time required for staple 50 to corrode and become absorbed in the body, even if moisture were to enter the package containing the device and staple 50.

In a fifth embodiment of the present invention (not shown in the Figures), a preferential corrosion zone can be created on a surgical staple by locally work hardening a portion of the staple, such as the crown, to create an area that is more anodic and susceptible to corrosion than the rest of the staple. The work hardening (also referred to as strain hardening) causes lattice strains and other material, causing a "little anode, big cathode" configuration, and resulting in rapid local corrosion in the work hardened area.

We have shown numerous alternate embodiments of the present invention, but it will be obvious to those skilled in the art that such embodiments are only examples, and that there are numerous variations and substitutions possible without departing from invention. It will also be understood that various features and element of the claimed invention can be alternatively described in terms of a means for performing the function provided by the feature and/or element. We intend that the invention be limited only by the spirit and scope of the appended claims.

We claim:

1. A surgical staple having a solid crown, a first solid leg, and a second solid leg, the surgical staple formed of a single metallic composition that corrodes in tissue of a patient, said surgical staple having at least one metallic preferential corrosion zone associated with the crown and the crown adapted to corrode within the patient more quickly than a different portion of the surgical staple corrodes within the patient, said surgical staple further comprising a non-metallic buttress that is deployable together and in physical contact with said surgical staple into tissue, said preferential corrosion zone comprising an interface between said surgical staple and said buttress; and wherein said buttress contains a corrosion promoting material that increases the electrochemical corrosion rate in the preferential corrosion zone of the surgical staple, wherein when the surgical staple is deployed into tissue the staple is formed into generally B-shaped configuration such that the first and second legs each curl inward, and wherein the preferential corrosion zone is in the crown, and wherein once the preferential corrosion zone is corroded the surgical staple is fragmented into first and second half-B-shape fragments.

2. The surgical staple of claim 1, wherein said preferential corrosion zone comprises an indentation that provides a site for crevice corrosion.

3. The surgical staple of claim 1, wherein said surgical staple develops said preferential corrosion zone during deployment of said surgical staple into tissue.

4. The surgical staple of claim 3, wherein said preferential corrosion zone comprises a coating, and wherein the coating develops a plurality of cracks during deployment of said surgical staple.

5. The surgical staple of claim 1, wherein said buttress is cathodic with respect to said surgical staple, and said surgical staple galvanically corrodes at an interface between said buttress and said surgical staple.

6. The surgical staple of claim 1, wherein said single metallic composition is commercially pure iron.

7. The surgical staple of claim 1 wherein said single metallic composition comprises iron and about 0.3 to 0.85 percent by weight carbon.

8. The surgical staple of claim 1, wherein said single metallic composition comprises iron and about 0.85 to 2 percent by weight carbon.

9. A surgical staple comprising: a crown, a first leg, a second leg; wherein the crown, first leg, and second leg are formed of a single metallic composition comprising iron, and wherein the crown comprises a solid metallic preferential corrosion zone adapted to corrode within the patient more quickly than a different portion of the surgical staple corrodes within the patient; and a non-metallic buttress deployable together with and in physical contact with the surgical staple, wherein said buttress contains a corrosion promoting material that increases the electrochemical corrosion rate in the preferential corrosion zone of the surgical staple, wherein when the surgical staple is deployed into tissue the staple is formed into generally B-shaped configuration such that the first and second legs each curl inward, and wherein the preferential corrosion zone is in the crown. and wherein once the preferential corrosion zone is corroded the surgical staple is fragmented into first and second half-B-shape fragments.

10. A surgical staple comprising: a crown; a first leg; a second leg wherein the crown, the first leg, and the second leg are formed of a single metallic composition that corrodes in tissue of a patient, said surgical staple having at least one metallic preferential corrosion zone in the crown adapted to corrode within a patient more quickly than a different portion of the surgical staple corrodes within the patient, wherein when the surgical staple is deployed into tissue the first and second legs each curl inward to form a generally B-shaped configuration, and wherein once the preferential corrosion zone is corroded the surgical staple is fragmented into first and second half-B-shape fragments, wherein the preferential corrosion zone is solid, and further comprising a buttress adjacent the preferential corrosion zone, the buttress comprising a corrosion promoting material that increases the electrochemical corrosion rate in the preferential corrosion zone of the surgical staple.

11. The surgical staple of claim 10, wherein the preferential corrosion zone comprises an indentation that provides a site for crevice corrosion.

\* \* \* \* \*